United States Patent [19]

Ringrose et al.

[11] Patent Number: 4,668,636
[45] Date of Patent: May 26, 1987

[54] ANALYTICAL ASSEMBLY USABLE IN APPARATUSES FOR OPTICALLY DETERMINING SPECIES IN SOLUTION

[75] Inventors: Anthony Ringrose, Chene-Bougeries; Ranald M. Sutherland, Geneva; Claus Dahne, Onex; John F. Place, Geneva, all of Switzerland

[73] Assignee: Battelle Memorial Institute, Geneva, Switzerland

[21] Appl. No.: 793,345

[22] Filed: Oct. 31, 1985

[30] Foreign Application Priority Data

Nov. 6, 1984 [CH] Switzerland ............... 05307/84

[51] Int. Cl.$^4$ ............... G01N 21/03; G01N 21/12; G01N 21/75; G01N 33/552
[52] U.S. Cl. ............... 436/164; 356/246; 422/58; 422/64; 422/102; 422/104; 436/527; 436/805; 436/807; 436/810
[58] Field of Search ............... 422/64, 65, 66, 58, 422/102, 104, 72; 356/244, 246, 440; 436/805, 807, 810, 527, 164; 248/49

[56] References Cited

U.S. PATENT DOCUMENTS 3,233,383  2/1966  Salm ............... 248/49 X
3,939,350  2/1976  Kronick et al. .
3,994,171  11/1976 Schwartz ............... 422/64 X
4,050,895  9/1977  Hardy et al. .
4,349,510  9/1982  Kolehmainen et al. ............... 422/66
4,406,547  9/1983  Aihara .
4,427,294  1/1984  Nardo ............... 422/64 X

FOREIGN PATENT DOCUMENTS

WO81/00912  4/1981  PCT Int'l Appl. .
WO83/01112  3/1983  World Int. Prop. O. .

OTHER PUBLICATIONS

Analytical Chemistry, vol. 45, No. 4, Apr. 1973, N. Harrick et al, "Multiple Internal Fluorescence Spectrometry", pp. 687–689.
Laser Focus, vol. 15, No. 8, Aug. 1979, "Internal Reflection Spectroscopy", see pp. 60–65.

Primary Examiner—Arnold Turk
Attorney, Agent, or Firm—Cushman, Darby & Cushman

[57] ABSTRACT

An apparatus responsive to optical changes in a waveguide when the latter is contacted with an analyte capable of reacting with a specific reactant thereto attached to the surface of said guide involves, for containing the analyte, an interchangeable round bottomed cuvette temporarily held by a suitably shaped carrier in working relationship with the optical components of the apparatus, this arrangement ensuring a correct optical orientation thereof relative to said component whatever the exact positioning of the cuvette.

7 Claims, 3 Drawing Figures

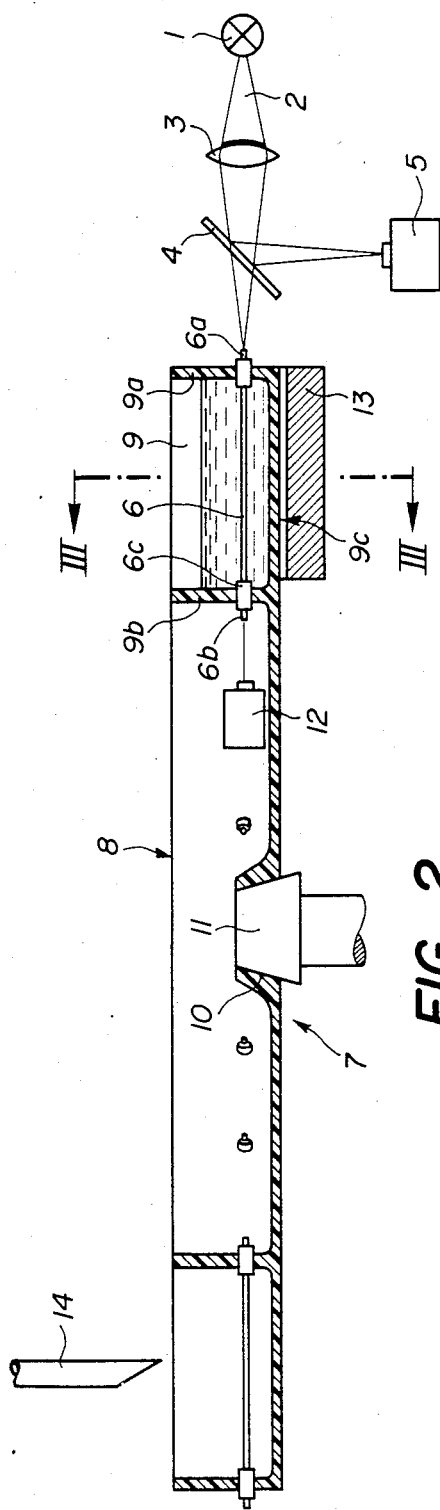
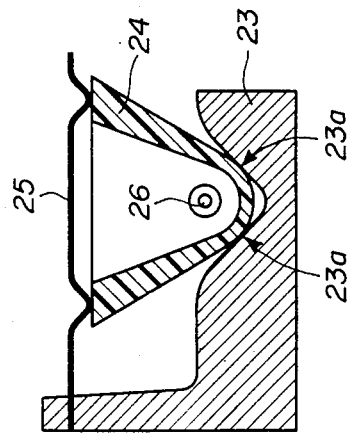
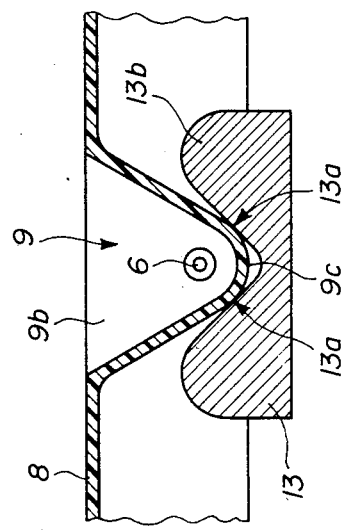
FIG. 1
FIG. 2
FIG. 3

ANALYTICAL ASSEMBLY USABLE IN APPARATUSES FOR OPTICALLY DETERMINING SPECIES IN SOLUTION

The present invention concerns an assembly including an analytical cuvette and supporting means thereto usable in an apparatus for optically determining species in solution, more especially for determining bioactive species by reactions of the immunoassay type.

Analytical apparatuses comprising optical fiber probes which can optically monitor the adsorption of chemical species on the fiber core are known. This technique is based on the immersion of a lit optical waveguide, for instance an optical fiber without cladding, in a test solution the refractive index of which is lower than that of the fiber core, whereby an interaction takes place between the evanescent wave component of the signal travelling along the waveguide and some species in solution to be determined. This approach is particularly interesting for monitoring events in the reaction space in close vicinity to the fiber, i.e. within reach of the evanescent wave component (a few tenths or hundredths of angstroms), this being in the case of tests based on the reaction of a first partner in a complexation reaction, this partner being adsorbed or attached on the probe surface, with a second partner dissolved in the sample solution.

Apparatuses suitable for such types of measurements have been recently disclosed in the following references WO84/00817; U.S. Pat. No. 4,447,546 (HIRSCHFELD et al); GB No. 2,103,786 (ICI); J. D. ANDRADE et al. Applied optics 23(11) 1984, 1812–1815; WO-A-8100912 (BUCKLES); U.S. Pat. No. 4,050,895 (HARDY et al); U.S. Pat. No. 3,939,350 (KRONICK et al).

Recently, there has been disclosed (see EP-A-75353) an apparatus for measuring parameters in a reaction of an analyte with a specific reactant thereto, said reaction occurring on the surface of a waveguide, e.g. a piece of optical fiber, and causing detectable changes to the optical properties thereof, which comprises a light source, means to inject a signal from that source into the input of said waveguide, detecting means to detect the light signal having undergone changes when travelling therethrough and emerging therefrom and converting it to an electric signal, and means for processing said signal into useful data pertaining to said reaction. This apparatus comprises:

(a) A fiber optic, the central part of which passes through a container or cuvette for holding a liquid analyte to be determined; the cladding of the fiber section immersed in the liquid has been removed so that this section can be coated, before operation, with a thin film of a specific complexing reagent of the species dissolved in the liquid and which should be determined. The assembly of the fiber and the holder constitutes the test probe of the apparatus.

(b) A light source, a collimating lens, an annular aperture and a focusing lens for injecting into the probe fiber core a light beam originating from the source and directed by the focussing lens at a selected angle to ensure propagation of the beam by multiple reflections in the probe fiber.

(c) The disclosed apparatus further comprises a main detector for transforming the exit light signal from the output end of the core into an electric signal, amplifying and computing circuits to process the signal from the detector and, finally, a display device providing the desired read-out output.

In addition to the above documents, U.S. Pat. No. 4,406,547 should also be mentioned which discloses an apparatus for the automatic analysis of biological samples which holds a number of cuvettes disposed peripherally on a turntable operated step by step.

Although the previously disclosed waveguide probe and cuvette assembly for performing the chemical reaction to be monitored have been operated satisfactorily in the past, it was found desirable to provide other systems which can be set-up faster, easier to operate and which can be constructed more economically. Also the present market demands cuvette and probe systems which can be provided by simple means from cheap materials and which can be discarded after use.

The present assembly, as defined in claim 1 is a solution to the afore-mentioned wishes. One embodiment of this assembly and an apparatus in which it can be incorporated as well as a modification will now be described with reference to the annexed drawing.

FIG. 1 is a schematic cross-sectional simplified view of an assembly according to the invention.

FIG. 2 is a schematic cross-sectional view of an analytical apparatus involving the use of a variant of the assembly of FIG. 1.

FIG. 3 is a schematic view in cross-section along line III—III of FIG. 2 of a detail of the apparatus of FIG. 2 at an enlarged scale.

The assembly shown in FIG. 1 comprises a cuvette 24 resting in a V-shaped groove of a carrier 23 and in contact with the walls thereof by two generants 23a of its bottom surface. The cuvettes of this embodiment are handled manually and slipped in correct position in the recess of carrier 23 as shown in the drawing; there, they are held in place by a spring 25. In this embodiment, the cuvette 24 has a rounded bottom in the form of a portion of cylinder and a waveguide 26 is located at the center of the radius of curvature of this partially cylindrical bottom such as to ensure that its alignment relative to the optical means involved (which are not shown but similar to those disclosed hereafter remain accurate even if, for some reason, the cuvette is slightly tilted sidewise in the holder. In this embodiment, the filling of the cuvette is done automatically with a dispenser (not shown) over the cuvette or, more commonly, by hand with a pipette. The operation of this assembly will be disclosed in connection with that of an apparatus in which this embodiment can be incorporated.

It should be noted in regard to this embodiment that the holding means for accurately maintaining the waveguide of the cuvette in a correct optical orientation relative to the light injecting and detecting means, said holding means being one of the key factors of the present invention, are important not only in connection with a casual tilting of one particular cuvette but also for allowing the use of a full series of interchangeable cuvettes with identically rounded bottom and identically centered waveguide. Exept for such construction criteria, the cuvettes may slightly differ in shape or in height, such possible variation being easily compensated by the spring means 25.

The apparatus represented in FIGS. 2 and 3 comprises an excitation light source 1 providing a light beam 2 to be focussed by a focussing means 3 and split by a beam splitter 4 into a reference beam directed to a reference detector 5 and a test beam to be injected into the input end 6a of a waveguide 6. The present apparatus comprises a vat shaped disk 7 with a shouldered edge 8 carrying a plurality of molded cavities 9 which constitute the cuvettes to be filled with the solution of analytes to be analyzed with the present apparatus. The disk 7 is made of a plastic having sufficient strength, flexibility and resilience to accept temporary bending deformation and easily return to its original shape when the bending force is relieved. Plastics such as PVC, polythene, polystyrene and others are convenient.

The disk 7 is pierced at the center with a tapered hole 10 to be adapted to the top of a shaft 11 conically shaped so as to match with the taper of hole 10. The shaft 11 is rotatable (by means of a motor not shown) which makes it possible to drive disk 7 horizontally into rotation.

Each cuvette 9 is provided with a piece of optical fiber 6 (waveguide) with both ends fitted through each opposite radial walls 9a, 9b thereof, such ends protruding externally from the cell, or being flush with the outside surface thereof, and constituting an input end 6a and an output end 6b, respectively of this waveguide. The inside portion of the fiber 6 to be immersed in the analyte solution is unclad so as to enable the evanescent wave component of the exciting wave signal travelling by multiple reflections through the guide to interact with the analyte in close vicinity thereto, i.e. a few tenth to a few hundredths of angstroems. At the places where the fiber 6 crosses the walls 9a and 9b of the cuvette, the fiber is provided with a cladding 6c this being so to prevent undesirable optical effects of the plastic of the walls on the signal carried by the fiber.

The present apparatus further comprises positioning means for the cuvette adapted for accurately positioning the waveguide of each cuvette, in turn, in facing relationship to the focusing means 3 and a signal detector 12 located in a fixed position opposite the incident beam 2 with regard to the cuvette 9. This detector 12 is supported by supporting means (not shown) to the main frame of the apparatus also not shown.

The positioning means of the apparatus which, together with the cuvette constitute an assembly according to the invention comprise a V shaped carrier 13 whose slant walls support cuvette 9 on only two points 13a on both sides. This is made possible by virtue of the profile of the bottom 9c of cuvette 9 which is roundedly molded in the form of a portion of cylinder, as shown on the drawing, which ensures that such bottom only touches the walls of holder 13 at the two points 13a (or rather the two corresponding longitudinal generants extending on the length of the bottom 9c of the cuvette). Both input 6a and output ends 6b of the waveguide are accurately centered with regard to the radius of curvature of the rounded bottom 9c which ensures that casual sidewise tilting of the cuvette will not disturb the positioning of the waveguide relative to the incident beam and the detector.

The external surface of the two side portions 13b of the carrier 13 are rounded off such as to allow the cuvettes 9 to ride over said portions upon rotation of the disk 7, thus enabling to stepwise position each cuvette, in turn, in correct orientation relative to the light excitation and detecting means, this being possible due to the disc's elasticity. Therefore, the disc can be rotated by steps each of which corresponds to one cell 9 coming in turn in facing relationship to the optical means for performing an analysis of a solution introduced into said cell. Of course, other means to provide such stepwise motion are also possible. For instance a rigid disc with annular openings 9 and detachable cuvettes inserted into said openings would be a suitable modification, the stepwise motion being provided by a disc lifting mechanism (cam) of the driving attachment (shaft 11 and its driving motor) or any other mechanism known in the art.

The present apparatus also comprises means for filling the cuvette with the analyte solution to be tested. Such means are represented schematically in FIG. 1 by a pipette 14. This pipette can be operated manually or automatically by means of a metered dispensing mechanism not represented which enables to introduce a well determined quantity of liquid into each cuvette at a selected time. Naturally, such a dispensing means needs not be located in relation to a cuvette remote from the measuring outfit as shown in the drawing. Actually, the pipette could be located immediately over the cell when in correct position for analysis, the analyte being added just before making the measurements.

The present apparatus further comprises means for processing the electric signals provided in response to the test beam and reference beam, by detectors 5 and 12. Such means comprise, as usual, amplifying, computing and displaying circuits providing the required information, such elements being in full conformity with the state of the art and described in detail in the literature (see also the above mentioned reference).

Under usual conditions, the present apparatus is operated as follows: a disc 9 is selected with the fiber waveguides inserted at the right place in each cell. Such insertion can be made manually by pushing the fibers into holes premanufactured in the radial walls of the cell pieces; for this, optical fibers whose central cladding has been removed by usual means are suitable. Alternatively, the waveguides can be made integral with the disc by molding procedures. In such case, the refractive index of the plastic used for the disc will preferably be lower than that of the waveguide fiber, the latter being a moldable plastic or glass pieces settled at the correct position within the cuvette during the molding operation.

The fibers are coated altogether or individually with a layer of a reactant specific to the analyte by usual means, for instance by the means disclosed in EP-A-75353 and the disc is placed in some initial position over shaft 11. Then after a first analyte solution has been poured into a first cuvette 9, the latter is put in place relative to the energized optical means 1, 3 and 12 by rotating the disc stepwise and the output signal from the waveguide is monitored by the means described above. While the reaction between the analyte and its specific reactant attached to the guide takes place, the beam of light in the fiber undergoes corresponding absorption and/or scattering which affects the output as a decrease in the output signal or as the generation of a fluorescent signal in case the compound formed in the reaction fluoresces under the excitation of the incident light.

Whatever the process taking place, the result is a change in the optical output from the guide and the correspondingly detected electric signal is processed and recorded as usual on the display to provide the required data on the analyte.

When the full series of analysis corresponding to each cuvette is terminated, the disc can be discarded and replaced by a new one.

We claim:

1. Analytical assembly for optically analyzing species in solution comprising:
    a cuvette having:

an elongated rectilinear waveguide of optical fiber with input and output ends, and a bottom;

an external surface on the bottom of said cuvette having a rounded profile of a portion of a cylinder whose axis coincides with that of the waveguide so that both input and output ends of said waveguide are accurately centered with regard to the radius of curvature of the rounded bottom;

a supporting means comprising a carrier having a positioning rectilinear groove having a V-shaped cross-section for supporting said rounded external surface of said cuvette by having said cuvette resting in contact with two longitudinal lines along said rectilinear groove of said supporting means.

2. Assembly as in claim 1 further comprising:

a light source for providing a light signal;

filling means for adding a solution to said cuvette;

a signal injecting means for injecting said light signal from said light source into said input end of said waveguide;

a signal detecting means for detecting said light signal emerging from said output end of said waveguide and for converting the light signal from said output end of said waveguide into an electrical signal;

a processing means for processing said electrical signal into useful data;

wherein said cuvette further comprises opposite radial walls for holding said solution in said cuvette so that said waveguide of said cuvette is immersed in said solution, a reaction occurs on the surface of the waveguide, and said reaction causes detectable changes to the optical properties of said light signal.

3. Assembly as in claim 2 further comprising:

a horizontally oriented disk-shaped multifunctional cuvette holder including:

a holding means having a plurality of said cuvettes, each cuvette being located radially side by side on the periphery of said disk-shaped cuvette holder and a rotating means for rotating said cuvettes stepwise;

whereby each cuvette will come, in turn, in said V-shaped rectilinear groove so that said input and output of its waveguide are accurately positioned in optical working relationship to said signal injecting and detecting means.

4. Assembly as in claim 3 wherein:

said V-shaped rectilinear groove of said carrier supporting means includes rounded off side portions so that when said disk-shaped holder is rotating stepwise said cuvettes can ride over said rounded off side portions, into said rectilinear groove of said supporting means, and out of said groove over said rounded off side portions;

said disk-shaped cuvette holder includes peripheral portions having resilient bending properties for bending of the peripheral portions when said cuvettes on said rotating disk-shaped cuvette holder come into contact with said supporting means.

5. A method for measuring parameters in a reaction in an analyte species in solution with a specific reactant thereto, in a device including a cuvette having a waveguide with input and output ends and a bottom, an external surface on the bottom having a rounded profile of a portion of a cylinder whose axis coincides with that of the waveguide so that the waveguide is accurately centered with regard to the radius of curvature of the rounded bottom, a light source, a supporting means having a rectilinear groove having a V-shaped cross section, a filling means, a signal injecting means, a signal detecting means, and a processing means, comprising the steps of:

providing a light signal;

placing said cuvette into said rectilinear groove of said supporting means relative to the other operational elements of the device in a position whereby said input and output ends of the said waveguide remain accurately oriented in optical relationship to said signal injecting and detecting means;

injecting said light signal from said light source into said input end of said waveguide of said cuvette;

adding a solution to said cuvette;

holding said solution in said cuvette so that said waveguide of said cuvette is immersed in said solution, a reaction occurs on the surface of the waveguide, and said reaction causes detectable changes to the optical properties of said light signal;

detecting said light signal emerging from said output end of said waveguide which has undergone changes when travelling through said waveguide;

converting said changed light signal to an electrical signal;

processing said electrical signal into useful data pertaining to said reaction.

6. Method as in claim 5 wherein said device further includes a horizontally oriented disk-shaped multifunctional cuvette holder including a holding means having a plurality of said cuvettes, each cuvette being located radially side by side on the periphery of said disk-shaped cuvette holder, a rotating means, and a positioning means, further comprising the steps of:

holding a plurality of cuvettes annularly;

and rotating said cuvettes stepwise to position each cuvette in turn in said V-shaped groove so that said input and output of its waveguide are accurately positioned in optical working relationship to said signal injecting and detecting means.

7. Method as in claim 6 wherein said supporting means of said device further includes rounded off side portions on the V-shaped carrier groove and said disk shaped cuvette holder further includes peripheral portions having resilient bending properties, further comprising the steps of:

riding the cuvettes over said rounded off side portions of said carrier groove when said disk-shaped cuvette is rotated stepwise; while simultaneously bending the resilient disk-shaped cuvette holder so that the cuvettes can move over the rounded off portions of said carrier groove into the V-shaped carrier groove and the said cuvettes can move out of said carrier groove and over said rounded off portions of said carrier so that said cuvettes can successfully exchange place one after another in the carrier groove.

* * * * *